United States Patent
Cheng et al.

(10) Patent No.: US 6,262,148 B1
(45) Date of Patent: Jul. 17, 2001

(54) PHENALKAMINE CURING AGENTS AND EPOXY RESIN COMPOSITIONS CONTAINING THE SAME

(75) Inventors: Chi-Wen Frank Cheng, New City; David Bender, Portchester; Hsing Tie Wang, Forest Hills, all of NY (US)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/334,085

(22) Filed: Jun. 16, 1999

Related U.S. Application Data

(60) Provisional application No. 60/091,467, filed on Jul. 1, 1998.

(51) Int. Cl.$^7$ ............................. C08K 3/20; C08L 63/02
(52) U.S. Cl. ........................ 523/458; 528/107; 564/373
(58) Field of Search ......................... 523/458; 564/373; 528/107

(56) References Cited

U.S. PATENT DOCUMENTS

| | | | |
|---|---|---|---|
| 4,188,312 | 2/1980 | Kempter et al. | 260/19 EP |
| 4,352,944 | 10/1982 | Tyman et al. | 568/766 |
| 4,399,268 | 8/1983 | Becker et al. | 528/99 |
| 4,444,634 | 4/1984 | Kempter et al. | 204/181 |
| 4,481,349 | 11/1984 | Marten et al. | 528/120 |
| 4,612,214 | * 9/1986 | Salvi | 427/136 |
| 5,025,078 | 6/1991 | Lucas et al. | 528/120 |
| 5,075,411 | 12/1991 | Ogawa et al. | 528/99 |
| 5,312,461 | 5/1994 | Farng et al. | 44/415 |
| 5,356,961 | 10/1994 | Nishimura et al. | 523/414 |
| 5,407,592 | 4/1995 | Cheng et al. | 252/51.5 |
| 5,569,536 | 10/1996 | Hunter et al. | 428/413 |
| 5,578,685 | 11/1996 | Neumann et al. | 525/481 |
| 5,608,029 | 3/1997 | Thaler et al. | 528/129 |
| 5,629,380 | 5/1997 | Baldwin et al. | 525/113 |
| 5,639,396 | 6/1997 | Thaler et al. | 508/544 |
| 5,688,905 | 11/1997 | Walker | 528/332 |

FOREIGN PATENT DOCUMENTS 2 152 925    8/1985   (GB).

OTHER PUBLICATIONS

Print Outs of Chem. Abstracts Reg. File Structures for Phenols Substituted with Cis–Aliphatic Groups, pvc Jun. 1999.*

Expoy Resin Chemistry Series 114, No. 9, Gardiner et al., Phenalkamines—"A New Class of Epoxy Curing Agents", pp. 98–114.

ASTM Designation:D 3363–92a "Standard Test Method for Film Hardness by Pencil Test" pp. 360 & 361.

ASTM Designation:D 3359–95 "Standard Test Methods for Measuring Adhesion by Tape Test" pp. 350–355.

ASTM Designation:D 2794–82 "Standard Test Method for Resistance of Organic Coatings to The Effects of Rapid Deformation (Impact)" pp. 520–522.

ASTM Designation:D 522–93a "Standard Test Methods for Mandrel Bend Test of Attached Organic Coatings" pp. 27–30.

Alkyd Resins, I., Purandare et al. "Modification with Cardanol–Hexamine Condensate", Abstract.

Encyclopedia of Chemical Technology, 4$^{th}$ edition, vol. 17, pp. 556, 568 & 579.

P. Gardner, "Drying Time/Gelation", pp. 1 & 2.

Derw. abst. 1970–76076R[41] of DE 2,025,159.

* cited by examiner

Primary Examiner—Robert Dawson
Assistant Examiner—D. Aylward
(74) Attorney, Agent, or Firm—Kristin H. Neuman; James H. Shalek; Lyon & Lyon, LLP

(57) ABSTRACT

The present invention relates to a compound according to formula (1)

$$[H_2N-R_{7-1c}^{R_{4-1c}}\underset{R_{5-1c}}{\overset{A}{|}}R_{6-1c}\underset{R_{1-1c}}{\overset{R_{2-1c}}{|}}N\underset{H}{\overset{H}{|}}C\underset{}{\overset{}{|}}]_c \overset{OH}{\underset{C_{15}H_{(31-n)}}{\bigcirc}}[\underset{H}{\overset{H}{|}}C\underset{R_{3-1a}}{\overset{R_{1-1a}R_{2-1a}}{|}}N\underset{H}{\overset{}{|}}R_{6-1a}\underset{R_{5-1a}}{\overset{A}{|}}R_{7-1a}-NH_2]_a$$
$$[\underset{R_{1-1b}}{\overset{H}{|}}C\underset{R_{3-1b}}{\overset{R_{2-1b}}{|}}N\underset{}{\overset{}{|}}R_{6-1b}\underset{R_{5-1b}}{\overset{A}{|}}R_{7-1b}-NH_2]_b$$

(1)

wherein n is 0, 2, 4 or 6 and a, b and c are, independently of one another, 1 or 0. $R_{1-1a}$, $R_{1-1b}$ and $R_{1-1c}$ are hydrogen, a hydrocarbyl containing 1 to 10 carbon atoms which are alkyl, aryl, alkylene, arylalkyl or alkylaryl or a hydrocarbyl containing 1 to 10 carbon atoms and at least one heteroatom which can be oxygen, sulfur or nitrogen. $R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ hydrogen or $C_1$–$C_4$alkyl. $R_{6-1a}$, $R_{7-1a}$, $R_{6-1b}$, $R_{7-1b}$, $R_{6-1c}$ and $R_{7-1c}$ are $C_1$–$C_4$akyl. A is an aromatic or alicyclic ring having 5 to 7 carbon atoms. The present invention further relates to a Mannich base reaction product obtained by combining an extract from cashew nutshell liquid with at least one aromatic or alicylic polyamine and at least one aldehyde compound, epoxy resin compositions and curable formulations containing the same, and methods for using such compositions.

22 Claims, 2 Drawing Sheets

PHENALKAMINE CURING AGENTS AND EPOXY RESIN COMPOSITIONS CONTAINING THE SAME

This application claim benefit to provisional application 60/091,467 Jul. 1, 1998.

The present invention relates to a novel class of phenalkamines and epoxy resin compositions containing the same wherein the cured coatings resulting therefrom have reduced Gardner color index. In particular, the novel phenalkamines are prepared via a Mannich base reaction sequence by reacting a selected phenol compound that is substituted with a carbonyl group containing compound and at least one selected aromatic or alicylic polyamine. The resulting phenalkamine can be used as a curing agent in epoxy resin compositions for coatings, finishes and varnishes.

BACKGROUND OF THE INVENTION

Mannich base reactions are well-known. Mannich base compounds are products based on the reaction of an aldehyde, generally formaldehyde, a phenolic compound and an amine. Various forms of phenolic compounds, amines and aldehydes have been proposed. Mannich base products are known to be suitable for curing epoxy resins.

Phenalkamine curing agents are a class of Mannich bases obtained by reacting a cardanol-containing extract derived from cashew nutshell liquid, an aldehyde compound, such as formaldehyde, and an amine. Commercially available phenalkamines use ethylenediamine and diethyltriamine as the amine. Phenalkamines are good epoxy resin hardeners for room temperature or low temperature curing applications. Phenalkamines, however suffer from the disadvantage that the cured epoxy articles are very dark in color (Gardner Color Index greater than 14), blushing and low mechanical properties. Due to the dark coloring of the cured coatings, epoxy resin compositions containing phenalkamine curing agents have been limited to use as primers and generally cannot be used as top coat material.

The extract from cashew nutshell liquid primarily contains a mixture of cardanol (I), cardol (II),

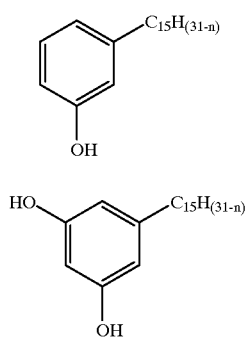

where n depends upon whether the side chain is saturated or unsaturated (n=0 for saturated, n=2 for monoene, n=4 for diene, and n=6 for triene), and related compounds of varying degrees of saturation. Numerous methods have been developed to purify the extract from cashew nutshell liquid with the stated goal of obtaining an isolated solution of cardanol. Typically, a purified extract solution will contain primarily cardanol with a minor amount of cardol.

SUMMARY OF THE INVENTION

The present invention relates to a novel phenalkamine compound according to formula (1)

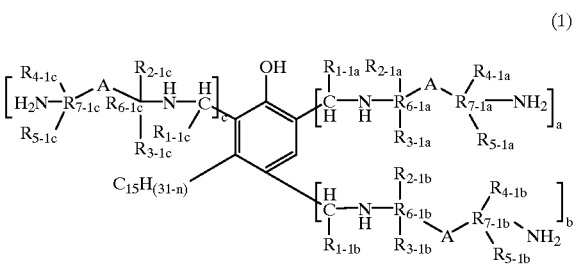

wherein n is 0, 2, 4 or 6, a, b and c are, independently of one another, 1 or 0, $R_{1-1a}R_{1-1b}$ and $R_{1-1c}$ are, independently of one another, hydrogen, a hydrocarbyl containing 1 to 10 carbon atoms which are alkyl, aryl, alkylene, arylalkyl or alkylaryl or a hydrocarbyl containing 1 to 10 carbon atoms and at least one heteroatom which can be oxygen, sulfur or nitrogen;

$R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ are independently of one another, hydrogen or $C_1$–$C_4$alkyl, $R_{6-1a}$, $R_{7-1a}$, $R_{6-1b}$, $R_{7-1b}$, $R_{6-1c}$ and $R_{7-1c}$ are, independently of one another $C_1$–$C_4$akyl; and A is an aromatic or alicylic ring having 5 to 7 carbon atoms. Preferably, $R_{1-1a}$, $R_{1-1b}$ and $R_{1-1c}$ are independently of one another, methyl, and a, b and c, independently of one another are 1 or 0. More preferably, $R_{1-1a}$ is hydrogen, a is 1 and b and c are 0.

$R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ are preferably, independently of one another, hydrogen, methyl or ethyl, and a, b and c, independently of one another are 1 or 0. More preferably, $R_{2-1a}$, $R_{3-1a}$, $R_{4-1a}$, and $R_{5-1a}$ are each hydrogen, a is 1 and b and c are 0. Most preferably, $R_{2-1a}$, $R_{3-1a}$, $R_{4-1a}$, and $R_{5-1a}$ are each hydrogen, a is 1 and b and c are 0.

$R_{6-1a}$, $R_{7-1a}$, $R_{6-1b}$, $R_{7-1b}$, $R_{6-1c}$ and $R_{7-1c}$ are preferably, independently of one another, methyl or ethyl and a, b and c, independently of one another, are 1 or 0. More preferably, $R_{6-1a}$ and $R_{7-1a}$ are methyl or ethyl, a is 1 and b and c are 0.

A is preferably an aromatic or alicyclic ring having 6 carbon atoms. More preferably, A is an aromatic or alicylic ring having 6 carbon atoms.

The present invention is a compound ideally represented by formulae (1a) or (1b):

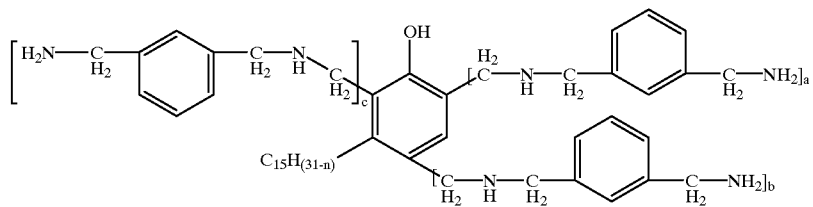

(1a)

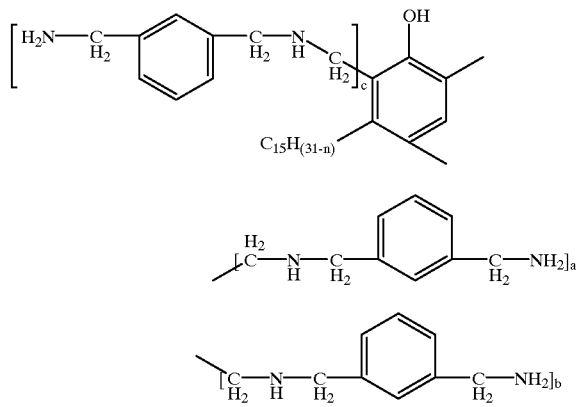

(1a)

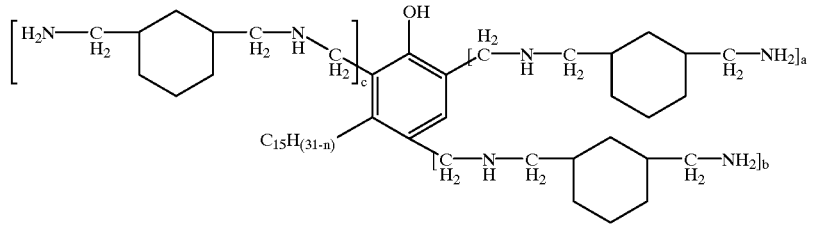

(1b)

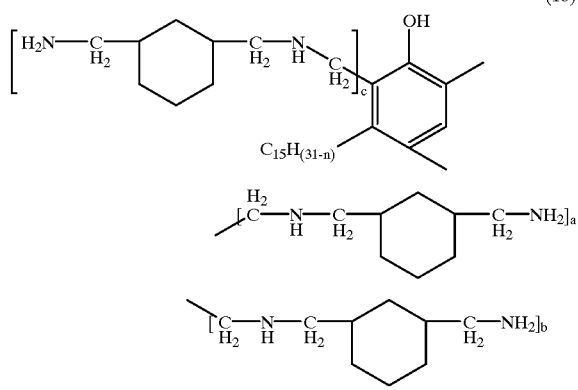

(1b)

wherein n, a, b and c have been defined above.

The present invention further relates to a Mannich base reaction product obtained by combining an extract from cashew nutshell liquid with at least one aromatic or alicylic polyamine and at least one aldehyde compound. The extract cashew nutshell liquid preferably contains a major portion of cardanol (I) and a minor amount of cardol (II)

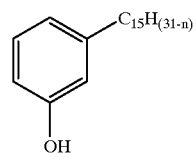

(I)

-continued

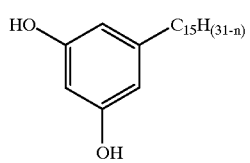
(II)

where n is 0, 2, 4 or 6. The extract cashew nutshell liquid preferably contains cardanol (I) and of cardol (II) in a weight ratio of about 90:10 to about 98:2. The Mannich base reaction product is preferably obtained by combining the extract and the at least one aldehyde compound with a polyamine selected from xylenediamine, 1,3-bis(aminomethyl)cyclohexane, and mixtures thereof. The Mannich base reaction product preferably comprises at least one compound ideally represented by structural formulae (1a) or (1b):

the present invention relates to an epoxy resin composition including a) a Mannich base reaction product described above and b) an epoxy resin having on average more than one glycidyl group per molecule.

The present invention further relates to a curable formulation including a) an epoxy resin composition containing the novel phenalkamine compound and an epoxy resin having on average more than one glycidyl group per molecule and b) a pigment. In the alternative, the present invention relates to a curable formulation including an epoxy resin composition containing a Mannich base reaction product and an epoxy resin having on average more than one glycidyl group per molecule and b) a pigment.

The present invention further relates to a method for coating a surface having reduced yellowness index using a phenalkamine-containing composition that comprises applying a curable formulation described above to the surface. In the alternative, the present invention relates to a method for coating a surface having reduced yellowness index using a Mannich base reaction product-containing (1a)

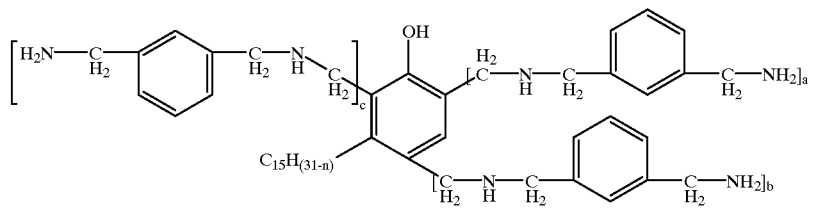

(1b)

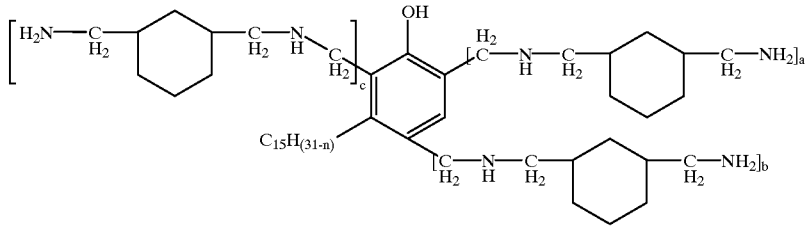

(1b)

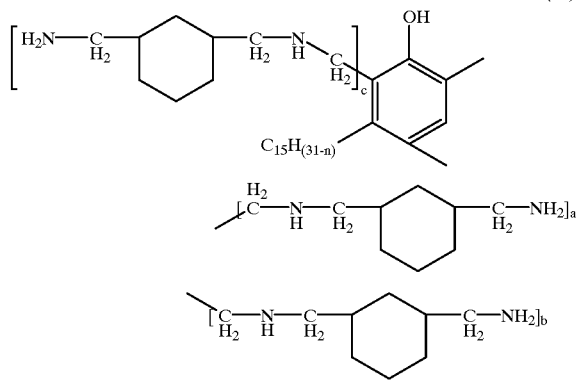

wherein n has been defined above, a, b and c, are, independently of one another, 1 or 0, and an average value for the sum of (a+b+c) is about 1.2 for all of the compounds corresponding to formulae (1a) and/or (1b) in said Mannich base reaction product mixture.

The present invention further relates to an epoxy resin composition including a) a novel phenalkamine compound described above and b) an epoxy resin having on average more than one glycidyl group per molecule. Alternatively, composition that comprises applying a curable formulation described above.

DETAILED DESCRIPTION OF THE INVENTION

Figure 1:
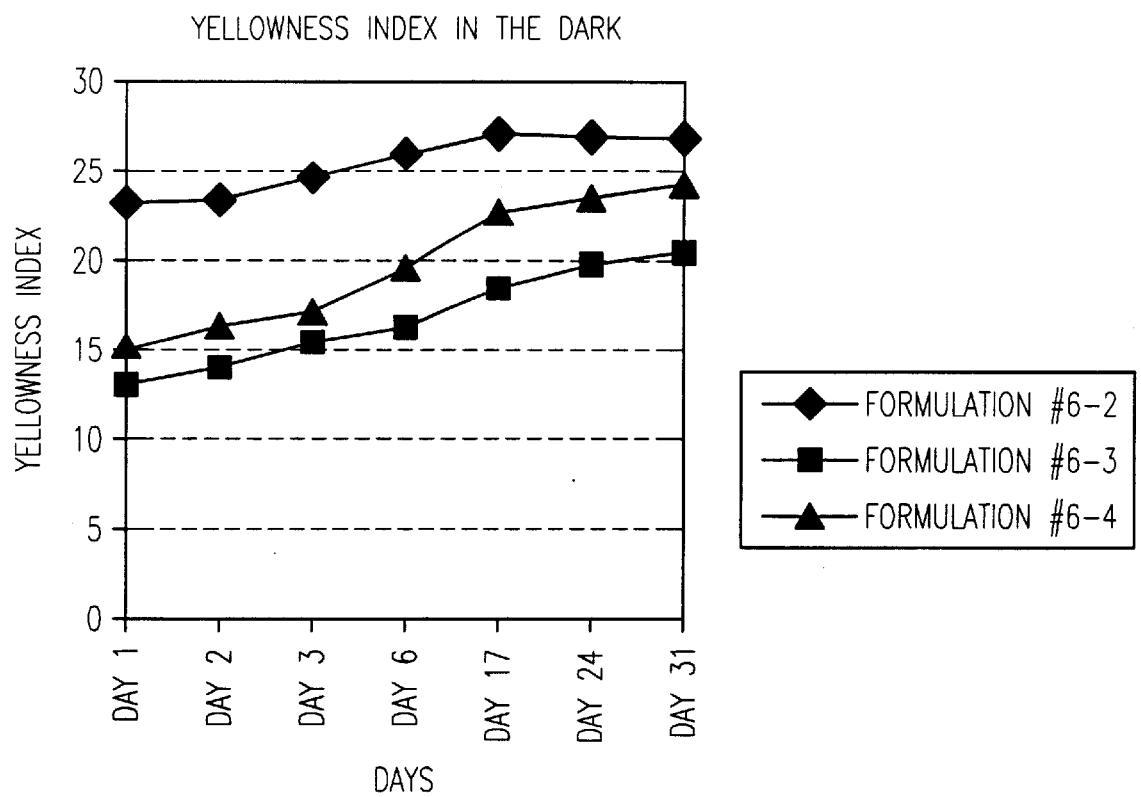
FIGS. 1 through 4 are graphs showing comparisons of the yellowness index for a group of coatings over a period of time.
Figure 2:
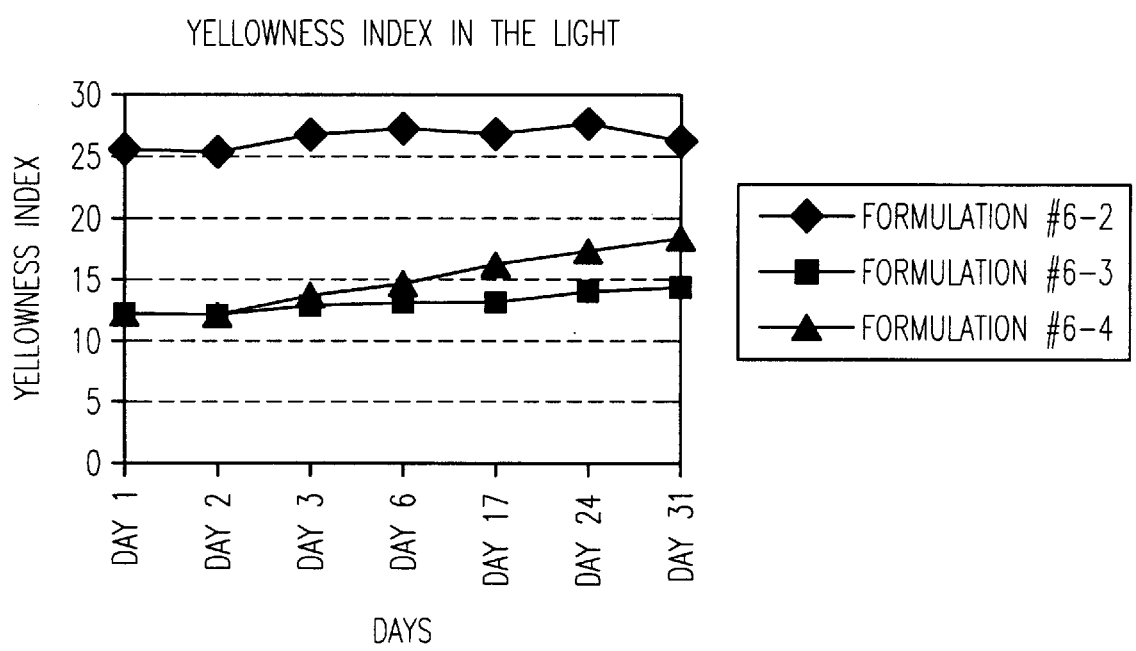
Figure 3:
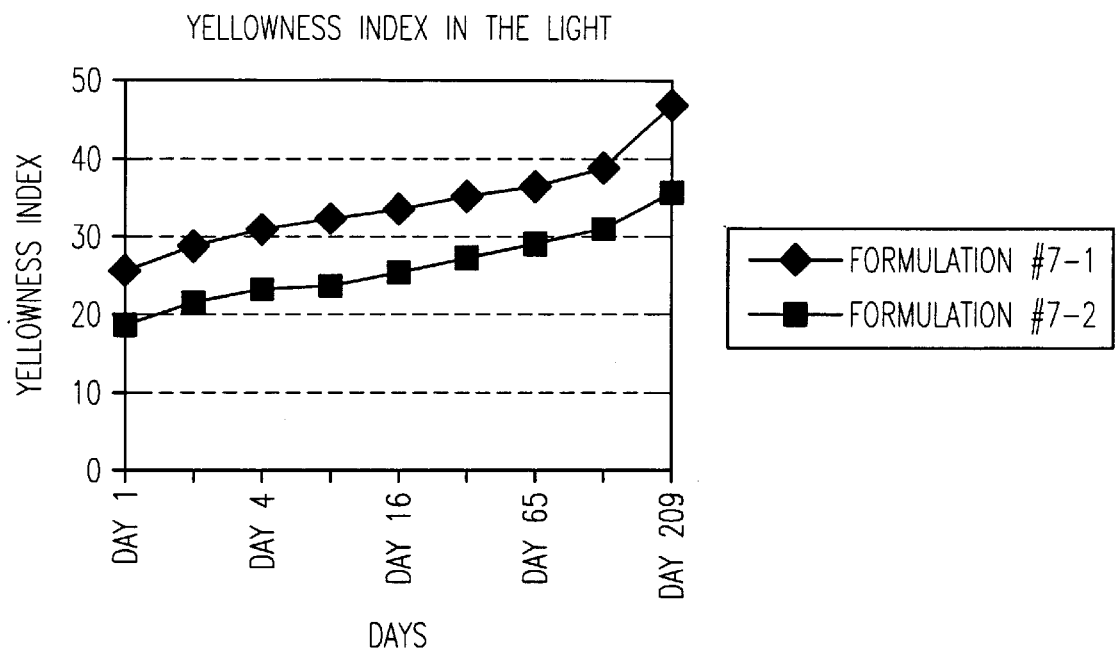
Figure 4:
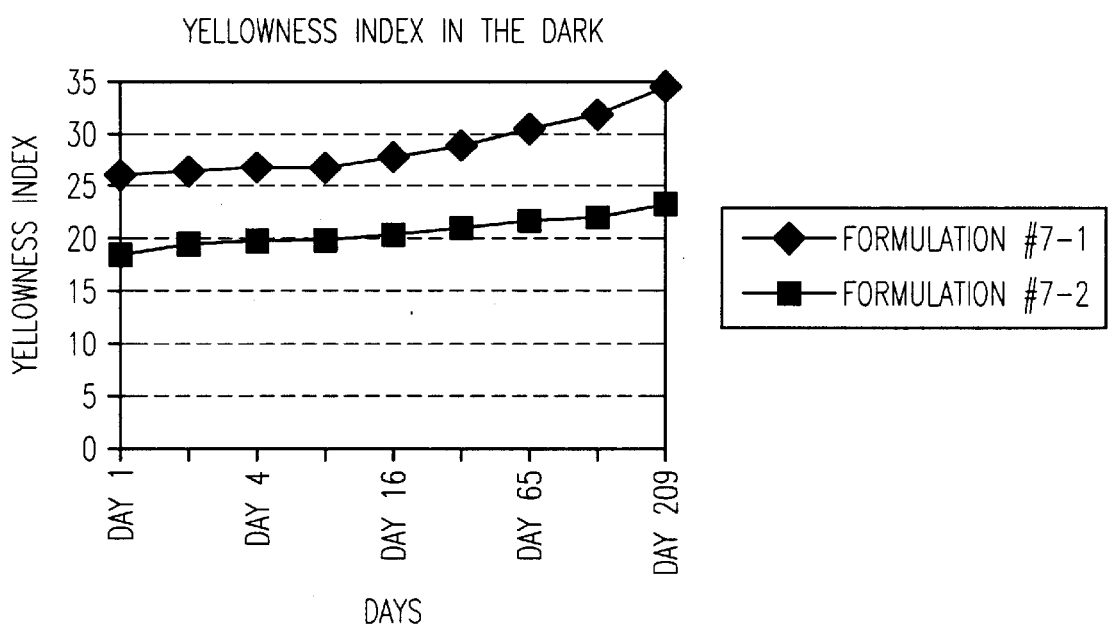

The novel Mannich base curing agents of the present invention can be prepared by reacting an extract derived from cashew nutshell liquid containing at least one phenolic compound with an aldehyde compound and at least one selected aromatic- or alicylic-polyamine, or mixtures thereof. The mole ratio of polyamine to phenolic compound is within the range of about 1:1 to about 10:1, more preferably from about 1:1 to about 4:1. The mole ratio of the polyamine to aldehyde compound is within the range of about 1:1 to about 5:1, preferably about 1:1 to about 2:1. On an equivalents basis, the ratio of aldehyde and amine should be more than or equal to one mole of amine per equivalent of the phenolic compound.

The polyamine and extract containing the phenolic compound are placed in a suitable vessel, and mixed thoroughly. The aldehyde compound is then added, either continuously over a period of time, or incrementally. The reaction is nearly spontaneous and fairly exothermic. Provisions for temperature control are necessary. After completion of aldehyde compound addition, water that is formed during synthesis is removed by distillation. Chemical reaction during synthesis is believed to involve electrophilic addition of the aldehyde to the phenolic compound to form an alkanolated phenol intermediate. Further condensation with the amine and elimination of water yields the Mannich base reaction product.

The liquid cashew nutshell extract solution, after heat treatment, contains a mixture of cardanol (I), cardol (II), and related low molecular weight compounds, wherein the mixture comprises a major portion of cardanol (I) and a minor amount, of cardol (II)

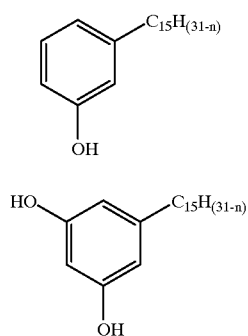

where n depends upon whether the side chain is saturated or unsaturated (n=0 for saturated, n=2 for monoene, n=4 for diene, and n=6 for triene), and related compounds of varying degrees of saturation. Preferably, the ratio of cardanol (I) relative to cardol (II) is about 90:10. The extract solution can be obtained by heat treatment of the cashew nutshell liquid or oil. Numerous methods have been developed to purify the extract from cashew nutshell liquid with the stated goal of obtaining an isolated solution of cardanol.

The extract solution can be purified by vacuum distillation to further reduce the amount of cardol in the extract solution. The crude cashew nutshell liquid is available in countries, such as Brazil and India. Palmer International Inc., which is located in Worcester, Pa., is a major importer of crude cashew nutshell liquid. The crude cashew nutshell liquid can be vacuum distilled using commercial distillation facilities to obtain a purified extract solution described above. Palmer is capable of producing such a purified extract solution containing at least about 85% by weight of a mixture containing a major portion of cardanol and a minor amount of cardol.

The aldehyde compound can be any compound containing the group (C=O) which occurs in aldehydes. These compounds can be characterized by the structural formula:

in which $R_1$ is hydrogen or a hydrocarbyl containing 1 to 10 carbon atoms which can be alkyl, aryl, alkylene, arylalkyl or alkylaryl. The hydrocarbyl groups can also contain 1 to 10 carbon atoms and at least one heteroatom which can be oxygen, sulfur or nitrogen. Typical aldehyde compounds are formaldehyde, butyraldehyde, heptaldehyde, hexadehyde, acetaldehyde, propionaldehyde, paraformaldehyde, benzaldehyde, salicylaldehyde and 2-ethylhexanal. Formaldehyde (in solution or as paraformaldehyde) is particularly preferred. These compounds are known in the art and are readily available from commercial sources or are easily made using known methods.

The polyamines used herein to produce the inventive compounds are selected from aromatic or alicyclic polyamines or mixtures thereof. The polyamine is preferably m-xylenediamine or liquid mixtures thereof with p-xylenediamine, and/or, 1,3- or 1,4-bis(aminoalkyl)cyclohexane or mixtures thereof. The aminoalkyl group is preferably an aminomethyl, aminoethyl, aminopropyl or aminobutyl, wherein the alkyl group is either a straight chain or branched. More preferably, the aminoalkyl group is aminomethyl or aminoethyl. The polyamine is particularly preferably m-xylenediamine alone, or in combination with p-xylenediamine, or 1,3-bis(aminomethyl)cyclohexane, which are commercially available from Mitsubishi Gas and Chemical, Tokyo, Japan.

The resulting novel Mannich base reaction product corresponds to a compound according to formula (1)

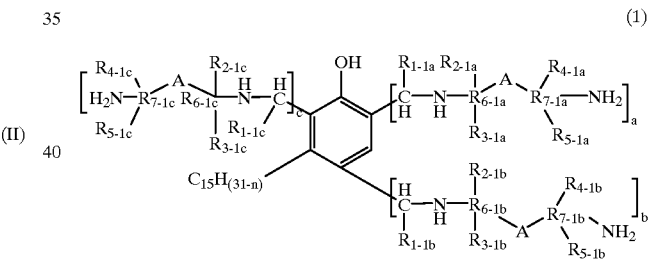

wherein n is 0, 2, 4 or 6, a, b and c are, independently of one another, 1 or 0, $R_{1-1a}$, $R_{1-1b}$ and $R_{1-1c}$ are, independently of one another, hydrogen, a hydrocarbyl containing 1 to 10 carbon atoms which are alkyl, aryl, alkylene, arylalkyl or alkylaryl or a hydrocarbyl containing 1 to 10 carbon atoms and at least one heteroatom which can be oxygen, sulfur or nitrogen;

$R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ are independently of one another, hydrogen or $C_1$–$C_4$alkyl, $R_{6-1a}$, $R_{7-1a}$, $R_{6-1b}$, $R_{7-1b}$, $R_{6-1c}$ and $R_{7-1c}$ are, independently of one another $C_1$–$C_4$akyl; and A is an aromatic or alicyclic ring having 5 to 7 carbon atoms.

A particularly preferred compound according to the present invention is derived from a reaction mixture containing formaldehyde as the aldehyde compound and xylenediamine or 1,3(bisaminomethyl)cyclohexane as the polyamine. Hence, a particularly preferred compound can be represented by the following idealized structural formulae (1a) and (1b):

(1a)
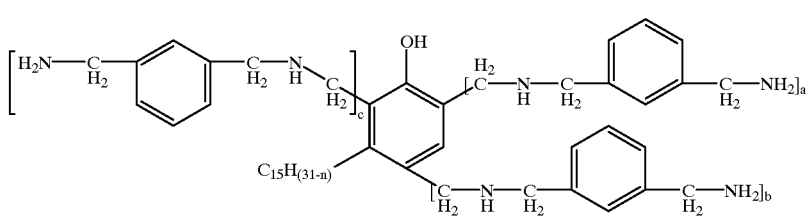

(1b)
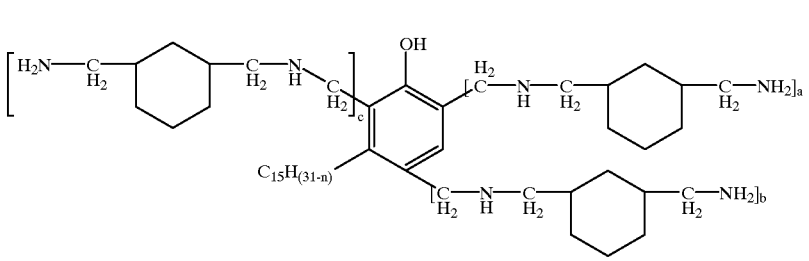

(1b)
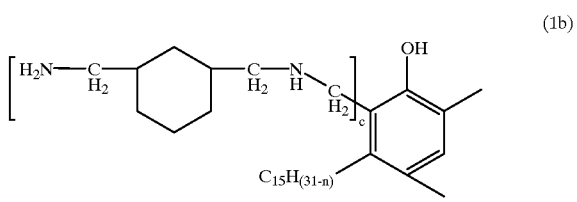
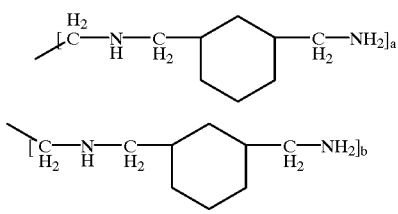

wherein n, a, b and c have been defined above.

The term "hydrocarbyl" as used herein encompasses any hydrocarbon radical, whether saturated, unsaturated, linear or cyclic subject to any other restrictions apparent from the text.

The novel compounds described above are obtained via a Mannich base reaction sequence using an extract of cashew nutshell liquid or oil. The cashew nutshell liquid can be obtained in varying degrees of purity. Accordingly, the novel compound will preferably be produced from a reaction mixture containing an extract having a major portion of cardanol (I) and a minor amount of cardol (II)

(I)
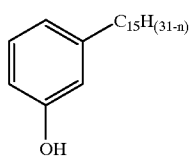

-continued (II)
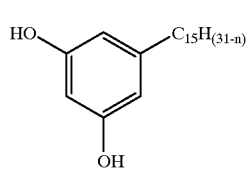

where n is 0, 2, 4 or 6.

A particularly preferred reaction mixture will contain said extract and at least one aldehyde compound, preferably formaldehyde, with a polyamine selected from xylenediamine, 1,3-bis(aminomethyl)cyclohexane, and mixtures thereof. The product mix of said reaction mixture will contain at least the following compounds ideally represented by structural formulae (1a) and (1b):

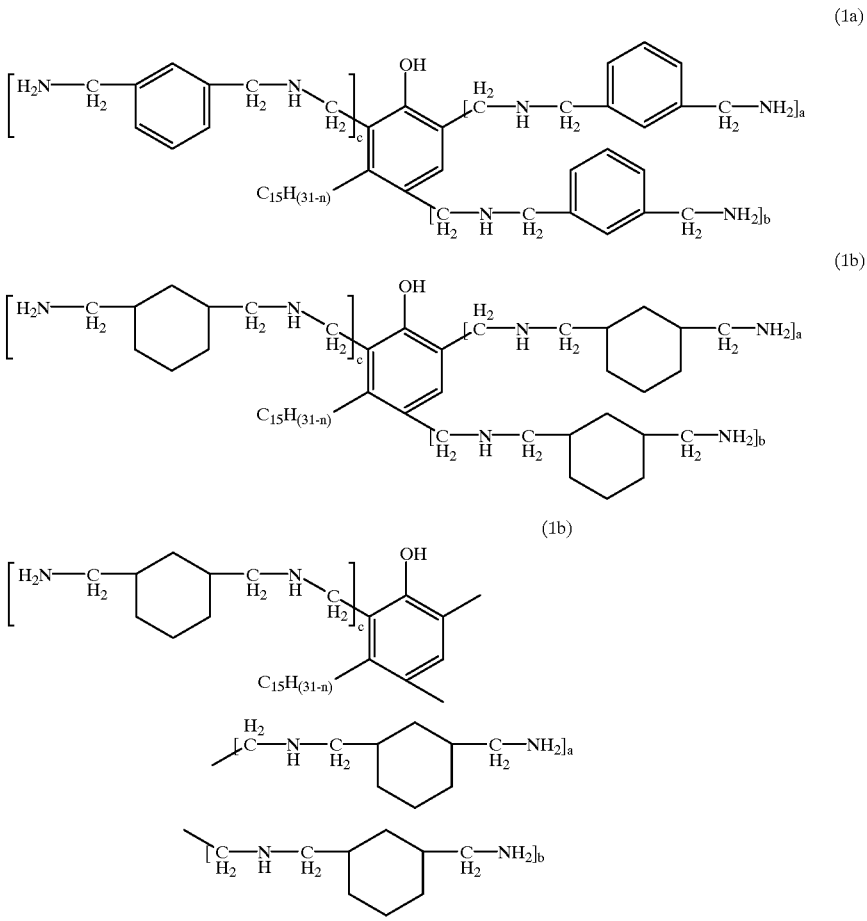

wherein n has been defined above and average value for the sum of (a+b+c) is about 1.2 based upon an average of all of the compounds corresponding to formulae (1a) and/or (1b) in said resulting product mix. The average value for the sum of (a+b+c) is determined from the molar ratio of the alkylated phenol to aldehyde to amine, which is most preferably 1:1.5:1.5.

The resulting Mannich base reaction products can be used as a curing agent for epoxy resin compositions. The epoxy resin can be any epoxy resin which can be cured by a Mannich base curing agent. Generally, the epoxy resin can be any curable epoxy resin having at least one glycidyl group per molecule. The epoxy resin can be saturated or unsaturated, linear or branched, aliphatic, cycloaliphatic, aromatic or heterocylic, and may bear substituents which do not materially interfere with the curing reaction. Such substituents can include bromine. The epoxy resin can be monomeric or polymeric, liquid or solid, but is preferably liquid at room temperature. Suitable epoxy resins include glycidyl ethers prepared by reacting epichlorohydrin with a compound containing at least one, preferably two or more, hydroxyl groups carried out under alkaline reaction conditions. Examples of epoxy resins suitable for use in the invention include polyglycidyl ethers of polyhydric phenols, epoxy novalacs or similar glycidylated polyphenolic resins, polyglycidyl ethers of alcohols, glycols or polyglycols, and polyglycidyl esters of polycarboxylic acids, and mixtures thereof.

The preferred epoxy resin is a resin based on a polyglycidyl ether of a polyhydric phenol. Polyglycidyl ethers of polyhydric phenols can be produced, for example, by reacting an epichlorohydrin with a polyhydric phenol in the presence of an alkali. Examples of suitable polyhydric phenols include: 2,2-bis(4-hydroxyphenyl)propane (bisphenol A); 2,2-bis(4-hydroxy-3-tert-butylphenyl) propane; 1,1-bis(4-hydroxyphenyl)propane; 1,1-bis(4-hydroxylphenyl)ethane; 1,1-bis(4-hydroxyphenyl) isobutane; bis(2-hydroxy-1-naphthyl)methane; 1,5-dihydroxynaphthalene; 1,1-bis(4-hydroxyphenyl)isobutane; 1,1-bis(4-hydroxy-3-alkylphenyl)ethane and the like. Suitable polyhydric phenols cans be obtained from the reaction of phenol with aldehydes, such as formaldehyde (bisphenol F). The preferred epoxy resin can be a mixture of the above resins. Particularly preferred epoxy resins are based on bisphenol A, such a GY 6010, available from Ciba Specialty Chemicals Corporation, Brewster, N.Y.

The preferred epoxy resins can also be blended with a glycidyl ether of an aliphatic or aromatic alcohol, glycol or polyglycol, or glycidylester of a monocarboxylic acid. Examples include butyl glycidyl ether, phenyl glycidyl ether, cresyl glycidyl ether, 1,4-buatanediol, diglycidyl ether, the glycidyl ester of neodecanoic acid, and the like. Such glycidyl ethers and esters can be blended with the preferred epoxy resins in concentrations of from about 1 to about 50% by weight in order to affect properties, such as wetting, viscosity, flexibility, and adhesion.

The preferred epoxy resin, which can be a mixture of the resins described above, can be combined with a curing system containing the novel Mannich base reaction product described above. The curing system can be combined with the epoxy resin at a temperature below the curing temperature. The preferred epoxy resin or curing system can be diluted with minor amounts of aliphatic or aromatic hydrocarbons, alcohols, or glycol ethers to facilitate handling and mixing requirements.

The epoxy resin composition can optionally further include other additives, such as flow control additives, antifoam agents, anti-sag agents, pigments, reinforcing agents, fillers, elastomers, stabilizers, extenders, plasticizers or flame retardants.

The resulting curable composition can be cured at a temperature within the range of from about −40° C., preferably from about −10° C., to about 150° C., for a sufficient time to fully cure the epoxy resin. For standard ambient cure applications, the composition is preferably cured at a temperature of from about −5° C. to about 40° C.

The epoxy resin composition described herein can be used as an adhesive, coating, flooring, casting or encapsulants, to name a few applications. The epoxy resin composition has particularly good applicability as a top coating, especially when combined with a pigment. The epoxy resin composition using the novel Mannich base reaction products described above can advantageously be combined with a pigment to produce a paint formulation having a reduced Gardner color index relative to currently available paint formulations containing phenalkamines. The resulting formulations can be applied in conventional manner by spray, roller or brush, for instance.

The novel Mannich base reaction products described above and particularly preferred methods for preparing and using said products are discussed more fully below in the following non-limiting examples.

EXAMPLE 1

Synthesis of Phenalkamine with m-xylenediamine

Charge 600 grams (2.0 moles) of cardanol (vacuum distilled cashew nutshell liquid to have a minimum purity of 85% cardanol and cardol, ratio of cardanol to cardol 92:8) obtained from Palmer International and 396 grams (2.9 moles) m-xylenediamine obtained from Mitsubishi Gas and Chemical, into a 2-liter, 3-necked round bottom flask equipped with a thermometer, a mechanical agitator, and a Dean-Stark water trap connected to a condenser. Then add 96 grams (3.20 moles of formaldehyde) of 92–94% paraformaldehyde (6–8% by weight water) (molecular weight 30) obtained from Aldrich Chemical Co. over a 20 minute period at a rate that maintains a temperature in the range of 80–100° C. A water bath can be used to maintain the desired temperature, particularly not in excess of 100° C., in the reaction vessel. Over a four-hour period, raise the temperature from 100° C. to 120° C. to remove and recover 52 grams of water in the water trap. The reaction completion can be monitored by way of an amine number titration, which shows 300–330 mg KOH/g. Upon completion, cool the pot temperature to 80 to 100° C. for discharge of 1040 grams of a clear red liquid having an amine value of 315 mg KOH/gram, Gardner color of 16, and a viscosity at 25° C. of 3,000 centipoise.

EXAMPLE 2

Synthesis of Phenalkamine with 1,3-bis(aminomethyl)cyclohexane

Charge 600 grams (2.0 moles) of cardanol (vacuum distilled cashew nutshell liquid) described above and 406 grams (2.9 moles) 1,3-bis(aminomethyl)cyclohexane obtained from Mitsubishi Gas and Chemical into a 2-liter, 3-necked round bottom flask equipped with a thermometer, a mechanical agitator, and a Dean-Stark water trap connected to a condenser. Then add 105 grams (3.50 moles of formaldehyde) of 92–94% paraformaldehyde (6–8% by weight water) (molecular weight 30) obtained from Aldrich Chemical Co. over a 20 minute period at a rate that maintains a temperature in the range of 80–100° C. A water bath can be used to maintain the desired temperature, particularly not in excess of 100° C., in the reaction vessel. Over a four-hour period, raise the temperature from 100° C. to 120° C. to remove and recover 56 grams of water in the water trap. The reaction completion can be monitored by way of an amine number titration (290–320 mg KOH/g). Upon completion, cool the pot temperature to 80 to 100° C. for discharge of 1055 grams of a clear red liquid having an amine value of 295 mg KOH/gram, Gardner color of 16, and a viscosity at 25° C. of 14,000 centipoise.

EXAMPLE 3

Blushing Test

The following formulations (amounts are in parts by weight unless stated otherwise) were prepared by mixing the resin and hardener components for about 2 minutes to produce a uniform paste.

| Component | Gardner Color | Formulation #3-1 | Formulation #3-2 | Formulation #3-3 | Formulation #3-4 |
| --- | --- | --- | --- | --- | --- |
| GY 6010 | <1 | 100 | 100 | 100 | 100 |
| HY3440 | 16 | 43.3 | | | |
| HY3441 | 16 | | 69.6 | | |
| Product of Example 1 | 16 | | | 69.6 | |
| Product of Example 2 | 16 | | | | 68 |

GY 6010 is an unmodified liquid epoxy resin based on bisphenol A and epichlorohydrin having a viscosity of 11,000 to 14,000 centipoise at 25° C. and an epoxy equivalent weight of about 182–192 grams per equivalent. GY 6010 is commercially available from Ciba Specialty Chemicals Corporation, Brewster, N.Y.

HY3440 is a phenalkamine based on an extract of liquid cashew nutshell liquid (85% purity with ratio of cardanol to cardol of 92:8) and formaldehyde wherein the polyamine is diethyltriamine.

HY3441 is a phenalkamine based on an extract of liquid cashew nutshell liquid (85% purity with ratio of cardanol to cardol of 92:8) and formaldehyde wherein the polyamine is ethylenediamine.

The resulting formulations were then coated as a 6 mil wet film onto a glass plate. The coated glass plates were cured in a refrigerator at 5° C. for 4 to 8 hours. The plates were then removed from the refrigerator and placed in a controlled environment at 25° C. overnight with the following results:

| Component | Formulation #3-1 | Formulation #3-2 | Formulation #3-3 | Formulation #3-4 |
| --- | --- | --- | --- | --- |
| Results | 5 | 4 | 1 | 0 | where on a scale of 0 to 5, 0 means no blush and 5 means worst blush.

EXAMPLE 4

The following formulations (amounts are in parts by weight unless stated otherwise) were prepared by mixing the resin and hardener components for about 2 minutes to produce a uniform paste.

| Component | Gardner Color | Formulation #4-1 | Formulation #4-2 | Formulation #4-3 | Formulation #4-4 |
|---|---|---|---|---|---|
| GZ9625 W90 | <1 | 100 | 100 | 100 | 100 |
| HY3440 | 16 | 31 | | | |
| HY3441 | 16 | | 49.8 | | |
| Product of Example 1 | 16 | | | 49.8 | |
| Product of Example 2 | 16 | | | | 48.6 |

GZ9625 W90 is an unmodified bisphenol A "Type 1/2" epoxy having a 90% solids content in an n-butanol solution and having an epoxy equivalent weight of about 500 grams per equivalent. GZ9625 W90 is commercially available from Ciba Specialty Chemicals Corporation, Brewster, N.Y.

The resulting formulations were then coated as a 6 mil wet film onto a glass plate. The coated glass plates were cured in a refrigerator at 5° C. for 4 to 8 hours. The plates were then removed from the refrigerator and placed in a controlled environment at 25° C. or 5° C. overnight to determine appearance. Tack-free and dry-through times were determined using Gardner drying time recorder. The tack-free time is the point in time when the ball scriber of the Gardner recorder penetrates the film and the groove exposes an underlying metal substrate. The dry-through time is the point in time in which the ball scriber can no longer make a groove on the film as evidenced by the end of the groove. Pencil hardness is determined by ASTM method No. D3363-92a. Cross-hatch adhesion is determined by ASTM method No. D3359-95. Impact is determined by ASTM method No. D2794. The Mandrel bend is determined by ASTM method No. D522-93a. Each of the above ASTM test methods are incorporated herein by reference.

| Component | Formulation #4-1 | Formulation #4-2 | Formulation #4-3 | Formulation #4-4 |
|---|---|---|---|---|
| Appearance at 5° C. | blush | slight blush | glossy | glossy |
| Appearance at 25° C. | slight blush | glossy | glossy | glossy |
| Tack-free at 25° C., hr. | 2 | 2.5 | 2 | 2 |
| Dry-through at 25° C., hr. | 3.5 | 3.5 | 3.5 | 4 |
| Tack-free at 5° C., hr. | 5 | 3 | 2 | 2.5 |
| Dry-through at 5° C. | 19 | 19 | 7 | 11 |
| Pencil Hardness | 4H | 2H | 2H | 2H |
| Cross Hatch adhesion (5 is best) | 5 | 5 | 5 | 5 |
| Impact (pass) direct, lb. | 24 | 24 | 20 | 10 |
| Impact (pass) reverse, lb. | 6 | 2 | 0 | 0 |
| Mandrel bend | pass | fail | fail | fail |

EXAMPLE 5

The following formulations (amounts are in parts by weight unless stated otherwise) were prepared by mixing the resin and hardener components for about 2 minutes to produce a uniform paste.

| Component | Gardner Color | Formulation #5-1 | Formulation #5-2 | Formulation #5-3 | Formulation #5-4 |
|---|---|---|---|---|---|
| GY 6010 | <1 | 100 | 100 | 100 | 100 |
| HY3440 | 16 | 43.3 | | | |
| HY3441 | 16 | | 69.6 | | |
| Product of Example 1 | 16 | | | 69.6 | |
| Product of Example 2 | 16 | | | | 68 |

| Component | Formulation #5-1 | Formulation #5-2 | Formulation #5-3 | Formulation #5-4 |
|---|---|---|---|---|
| Appearance at 5° C. | blush | slight blush | glossy | glossy |
| Appearance at 25° C. | slight blush | slight blush | glossy | glossy |
| Tack-free at 25° C., hr. | 3.5 | 3 | 3 | 3.5 |
| Dry-through at 25° C., hr. | 9.5 | 8.5 | 5.5 | 5 |
| Tack-free at 5° C., hr. | 5 | 4 | 4 | 5 |
| Dry-through at 5° C. | 23 | 19 | 14 | 13 |
| Pencil Hardness | 3H | B | 3H | 2H |
| Cross Hatch adhesion (5 is best) | 5 | 5 | 5 | 5 |
| Impact (pass) direct, lb. | 20 | 26 | 20 | 10 |
| Impact (pass) reverse, lb. | 0 | 0 | 0 | 0 |
| Mandrel bend | fail | pass | fail | fail |

EXAMPLE 6

The following formulations (amounts are in parts by weight unless stated otherwise) were prepared by mixing the resin, hardener and pigment components for about 2 minutes to produce a uniform paste.

| Component | Gardner Color | Formulation #6-1 | Formulation #6-2 | Formulation #6-3 | Formulation #6-4 |
|---|---|---|---|---|---|
| R28P-40 | | 100 | 100 | 100 | 100 |
| GZ9625 W90 | <1 | 15.5 | | | |
| HY3440 | 16 | 35.8 | | | |
| HY3441 | 16 | | 49.8 | | |
| Product of Example 1 | 16 | | | 49.8 | |
| Product of Example 2 | 16 | | | | 48.6 |
| Pigment/Binder | | 40/60 | 40/60 | 40/60 | 40/60 |

RP28P-40 is a white paint formulation containing 100 parts by weight of GZ9625 W90 and 93.2 parts by weight of titanium dioxide, TI-Pure, $R_{706}$, available from DuPont, Wilmington, Del. The resulting formulations were then coated as a 10 mil wet film onto a cool roll steel panel. The "in the light" panels are left on the laboratory bench and exposed to fluorescent light. The "in the dark" panels are stored in drawers to exclude any light. The coated steel panels were cured overnight at 22° C. and monitored for yellowness with the following results:

|  | Formulation #6-2 | Formulation #6-3 | Formulation #6-4 |
|---|---|---|---|
| In the Light |  |  |  |
| Day 1 | 23.28 | 13.16 | 15.12 |
| Day 2 | 23.47 | 13.99 | 16.58 |
| Day 3 | 24.64 | 15.49 | 17.32 |
| Day 6 | 25.94 | 16.43 | 19.66 |
| Day 17 | 26.99 | 18.56 | 22.85 |
| Day 24 | 26.75 | 19.93 | 23.59 |
| Day 31 | 26.82 | 20.53 | 24.3 |
| In the Dark |  |  |  |
| Day 1 | 25.43 | 12.13 | 12.26 |
| Day 2 | 25.31 | 11.98 | 12.39 |
| Day 3 | 26.68 | 12.99 | 13.9 |
| Day 6 | 27.11 | 13.17 | 14.73 |
| Day 17 | 26.61 | 13.12 | 16.31 |
| Day 24 | 27.44 | 14.07 | 17.32 |
| Day 31 | 26.14 | 14.47 | 18.53 |

EXAMPLE 7

The following formulations (amounts are in parts by weight unless stated otherwise) were prepared by mixing the resin, hardener and pigment components for about 2 minutes to produce a uniform paste.

| Component | Formulation #7-1 | Formulation #7-2 |
|---|---|---|
| R28P-20A | 100 | 100 |
| HY3441 | 49.8 |  |
| Product of Example 2 |  | 28.3 |
| Pigment/Binder | 40/60 | 40/60 |

RP28P-20A is a white paint formulation containing 363.6 grams of GY 6010, 400 grams of titanium dioxide (R-706), available from DuPont and 72.7 grams of n-butanol. The resulting formulations were then coated as a 10 mil wet film onto a cool roll steel panel. The coated steel panels were cured overnight at 22° C. and monitored for yellowness with the following results:

|  | Formulation #7-1 | Formulation #7-2 |
|---|---|---|
| In the Light |  |  |
| Day 1 | 26.07 | 18.71 |
| Day 2 | 29.06 | 21.57 |
| Day 4 | 31.03 | 23.08 |
| Day 8 | 32.17 | 23.88 |
| Day 16 | 33.48 | 25.35 |
| Day 31 | 35.31 | 27.70 |
| Day 65 | 36.75 | 29.10 |
| Day 110 | 38.81 | 31.06 |
| Day 209 | 46.54 | 35.74 |
| In the Dark |  |  |
| Day 1 | 26.07 | 18.71 |
| Day 2 | 26.52 | 19.64 |
| Day 4 | 26.77 | 19.89 |
| Day 8 | 26.95 | 19.99 |
| Day 16 | 27.88 | 20.49 |
| Day 31 | 28.98 | 21.03 |
| Day 65 | 30.72 | 21.63 |
| Day 110 | 31.88 | 22.18 |
| Day 209 | 34.53 | 23.45 |

Preferred embodiments of the present invention relating to novel phenalkamines, compositions thereof and methods for using the same have been described above. Those skilled in the art having the benefit of the teachings presented in the foregoing will recognize modifications and other embodiments. Therefore, it is understood that the invention is not limited to the specific embodiments disclosed herein, and that modifications and other embodiments are intended to be within the scope of the appended claims.

We claim:

1. A compound according to formula (1)

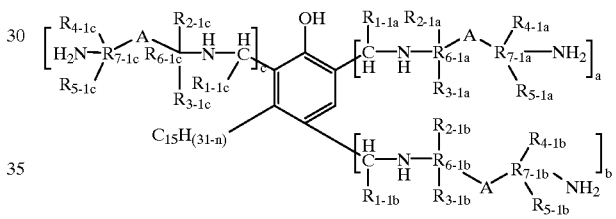

wherein n is 0, 2, 4 or 6, a, b and c are, independently of one another, 1 or 0, with the proviso that at least one of a, b or c is 1, $R_{1-1a}$, $R_{1-1b}$ and $R_{1-1c}$ are, independently of one another, hydrogen, a hydrocarbyl containing 1 to 10 carbon atoms which are alkyl, aryl, alkylene, arylalkyl or alkylaryl or a hydrocarbyl containing 1 to 10 carbon atoms and at least one heteroatom which can be oxygen, sulfur or nitrogen;

$R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ are independently of one another, hydrogen or $C_1$–$C_4$alkyl, $R_{6-1a}$, $R_{7-1a}$, $R_{6-1b}$, $R_{7-1b}$, $R_{6-1c}$ and $R_{7-1c}$ are, independently of one another $C_1$–$C_4$akyl; and A is an aromatic or alicyclic ring having 5 to 7 carbon atoms.

2. A compound according to claim 1 wherein $R_{1-1a}$, $R_{1-1b}$ and $R_{1-1c}$ are, independently of one another, hydrogen, methyl or ethyl, and a, b and c, independently of one another, are 1 or 0, with the proviso that at least one of a, b or c is 1.

3. A compound according to claim 1 wherein $R_{1-1a}$ is hydrogen, a is 1 and b and c are 0.

4. A compound according to claim 1 wherein $R_{2-1a}$, $R_{3-1a}$, $R_{4-1a}$, $R_{5-1a}$, $R_{2-1b}$, $R_{3-1b}$, $R_{4-1b}$, $R_{5-1b}$, $R_{2-1c}$, $R_{3-1c}$, $R_{4-1c}$ and $R_{5-1c}$ are, independently of one another, hydrogen, methyl or ethyl, and a, b and c, independently of one another, are 1 or 0, with the proviso that at least one of a, b or c is 1.

5. A compound according to claim 4 wherein $R_{2-1a}$, $R_{3-1a}$, $R_{4-1a}$, and $R_{5-1a}$ are each hydrogen, a is 1 and b and c are 0.

6. A compound according to claim 3 wherein $R_{2-1a}$, $R_{3-1a}$, $R_{4-1a}$, and $R_{5-1a}$ are each hydrogen, a is 1 and b and c are 0.

7. A compound according to claim 1 wherein $R_{6-1a}$, $R_{7-1a}$, $R_{6-1b}$, $R_{7-1b}$, $R_{6-1c}$ and $R_{7-1c}$ are, independently of one another, methyl or ethyl, and a, b and c, independently of one another, are 1 or 0, with the proviso that at least one of a, b or c is 1.

8. A compound according to claim 6 wherein $R_{6-1a}$ and $R_{7-1a}$ are methyl or ethyl, a is 1 and b and c are 0.

9. A compound according to claim 1 wherein A is an aromatic or alicyclic ring having 6 carbon atoms.

10. A compound according to claim 8 wherein A is an aromatic or alicylic ring having 6 carbon atoms.

11. A compound according to claim 1 represented by formulae (1a) or (1b):

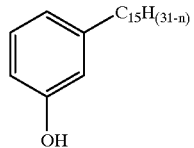
(I)

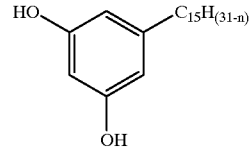
(II)

where n is 0, 2, 4 or 6.

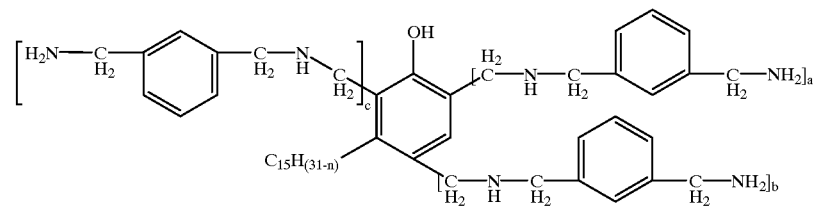
(1a)

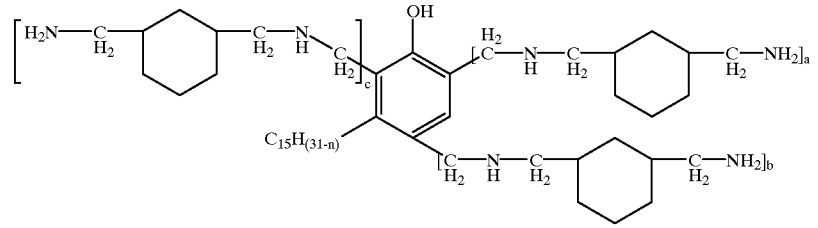
(1b)

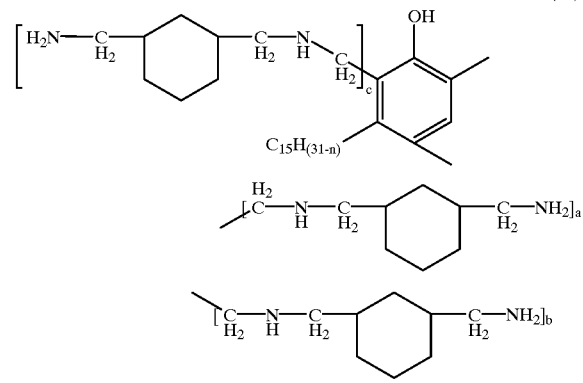
(1b)

wherein n, a, b and c have been defined above.

12. A Mannich base reaction product obtained by combining an extract from cashew nutshell liquid with at least one aromatic or alicylic polyamine and at least one aldehyde compound.

13. A Mannich base reaction product according to claim 12 wherein the extract cashew nutshell liquid contains a major portion of cardanol (I) and a minor amount of cardol (II)

14. A Mannich base reaction product according to claim 13 wherein the extract cashew nutshell liquid contains cardanol (I) and of cardol (II) in a weight ratio of about 90:10 to about 98:2.

15. A Mannich base reaction product according to claim 13 obtained by combining the extract and the at least one aldehyde compound with a polyamine selected from xylenediamine, 1,3-bis(aminomethyl)cyclohexane, and mixtures thereof.

16. A Mannich base reaction product according to claim 15 comprising at least one compound represented by structural formulae (1a) or (1b):

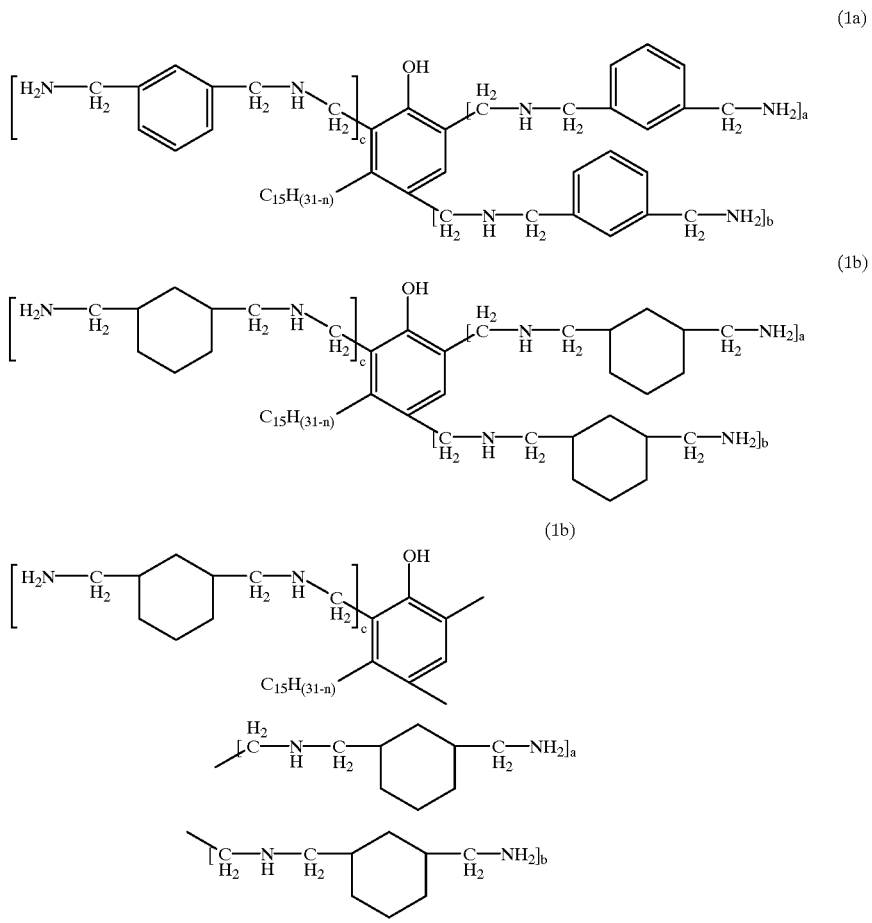

wherein n has been defined above, a, b and c, are, independently of one another, 1 or 0, and an average value for the sum of (a+b+c) is about 1.2 for all of the compounds corresponding to formulae (1a) and/or (1b) in said Mannich base reaction product mixture.

17. An epoxy resin composition comprising:
   a) a compound according to claim 1 and
   b) an epoxy resin having on average more than one glycidyl group per molecule.

18. An epoxy resin composition comprising:
   a) a Mannich base reaction product according to claim 16 and
   b) an epoxy resin having on average more than one glycidyl group per molecule.

19. A curable formulation comprising:
   a) an epoxy resin composition according to claim 17 and
   b) a pigment.

20. A curable formulation comprising:
   a) an epoxy resin composition according to claim 18 and
   b) a pigment.

21. A method for coating a surface having reduced yellowness index using a phenalkamine-containing composition that comprises applying a curable formulation according to claim 19 to the surface.

22. A method for coating a surface having reduced yellowness index using a phenalkamine-containing composition that comprises applying a curable formulation according to claim 20 to the surface.

* * * * *